(12) United States Patent
Fritz et al.

(10) Patent No.: US 6,616,616 B2
(45) Date of Patent: Sep. 9, 2003

(54) LANCET SYSTEM

(75) Inventors: Michael Fritz, Biblis (DE); Hans List, Hesseneck-Kailbach (DE); Thomas Weiss, Mannheim (DE); Frank Deck, Niederkirchen (DE); Herbert Argauer, Pirk (DE); Claudio Immekus, Mannheim (DE)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/963,967

(22) Filed: Sep. 26, 2001

(65) Prior Publication Data

US 2002/0120216 A1 Aug. 29, 2002

(30) Foreign Application Priority Data

Sep. 26, 2000 (DE) .......................................... 100 47 419

(51) Int. Cl.⁷ .................................................. A61B 5/00
(52) U.S. Cl. ...................................................... 600/583
(58) Field of Search .......................... 600/583; 606/181, 606/182, 183; 221/270, 271

(56) References Cited

U.S. PATENT DOCUMENTS

| | | | |
|---|---|---|---|
| 3,030,959 A | * 4/1962 | Grunert | ...................... 606/182 |
| 4,794,926 A | 1/1989 | Munsch et al. | |
| 5,029,583 A | 7/1991 | Meserol et al. | |
| 5,035,704 A | 7/1991 | Lambert et al. | |
| 5,152,775 A | 10/1992 | Ruppert | |
| 5,514,152 A | 5/1996 | Smith | |
| 5,569,287 A | * 10/1996 | Tezuka et al. | ............... 606/182 |
| 5,578,014 A | 11/1996 | Erez et al. | |
| 6,228,100 B1 | * 5/2001 | Schraga | ....................... 606/183 |
| 6,306,152 B1 | * 10/2001 | Verdonk et al. | ............. 606/182 |

FOREIGN PATENT DOCUMENTS

| DE | 19855465 A1 | 6/1999 |
|---|---|---|
| EP | 565 970 A1 | 10/1993 |

* cited by examiner

*Primary Examiner*—Max F. Hindenburg
*Assistant Examiner*—Jonathan Foreman
(74) *Attorney, Agent, or Firm*—Brinks Hofer Gilson & Lione (57) ABSTRACT

The invention concerns a lancet system comprising a plurality of essentially needle-shaped lancets, a drive unit which has a drive element which is moved from a resting position into a lancing position in order to carry out a lancing process, a storage area to store the lancets, a withdrawal area to guide at least the tip of the lancet out of the system during the lancing process and a transport unit which can transport lancets from the storage area into the withdrawal area, wherein the drive element is arranged in such a manner that in the withdrawal area it can act on the lancet located there to carry out a lancing process and thus move the lancet from a resting position into a lancing position and wherein the system has a retraction device in the withdrawal area which can interact with the lancet located in the withdrawal area in order to move the lancet after completion of the lancing process from the lancing position into the resting position and it concerns a lancet magazine adapted to the system, a corresponding lancing device and a working process for the system.

19 Claims, 9 Drawing Sheets

LANCET SYSTEM

BACKGROUND OF THE INVENTION

The invention concerns a system for storing and providing lancets for collecting body fluids, in particular for blood collection, and it concerns a corresponding working process for the system for the purpose of collecting body fluids and in particular for blood collection.

The examination of samples of body fluids and in particular blood samples in clinical diagnostics enables an early and reliable detection of pathological states and a specific and well-founded monitoring of body states. Medical blood diagnostics always requires the collection of a blood sample from an individual to be examined. Whereas several milliliters of blood are collected from a person to be examined by venipuncture for analysis in hospitals and by physicians in private practice in order to carry out many laboratory tests, nowadays only a few microliters of blood and sometimes even less is often sufficient for individual analyses which are specific for one parameter. Such small amounts of blood do not require venipuncture. On the contrary it is sufficient to obtain blood by pushing a sterile, sharp lancet through the skin e.g. into the finger pad or earlobe of the person to be examined in order to collect a few microliters of blood or even amounts of blood in the nanoliter range for the analysis. This method is particularly suitable when it is possible to carry out the analysis of the blood sample immediately after the blood collection.

Lancets and corresponding devices (so-called blood collection instruments, blood lancet devices or lancing devices) which enable a substantially pain-free and reproducible blood collection are available especially in the so-called home-monitoring field i.e. where medical laymen themselves carry out simple analyses of the blood especially for the regular blood collection by diabetics which has to be carried out several times daily to monitor the blood glucose concentration. Examples of lancets and lancing devices are the commercially available devices (lancing devices) and lancets Glucolet® from the Bayer AG Company and Softclix® from Roche Diagnostics GmbH. Such lancets and devices (lancing devices) are for example the subject matter of EP-A 0 565 970.

In the systems that are available at present the lancets for use in lancing devices are usually provided in a loose form. For each lancing process the user manually removes a lancet from a pack, for example a cardboard box or a tube containing a plurality of lancets (usually in a disordered arrangement and loosely packed). Subsequently the lancing device is prepared for receiving the lancet by for example unscrewing or pulling off a protecting cap to expose the lancet holder of the lancing device. The lancet removed from the pack is manually inserted into the lancet holder of the lancing device and fixed there. Then the protective cover has to be manually removed from the lancet. Subsequently the lancing device is sealed again with its protecting cap. The cap ensures that the lancet is no longer accessible from outside. It usually has an opening through which the lancet tip can pass during the actual lancing process. Finally the lancing device is tensioned and is available for the lancing process to collect blood.

The many manual operating steps in conventional lancet systems (lancet and lancing device) are felt to be disadvantageous by the user and are particularly problematic when perception is limited in a hypoglycaemic state. Moreover the user is not prevented from using a once inserted lancet several times for lancing and collecting blood. Multiple use of a lancet must be prevented for hygienic reasons especially when the lancet is used by more than one person which for example may be the case in doctors practices or hospitals or if misuse for example by children cannot be excluded. On the other hand the repeated use of lancets also leads to increasing pain for the user since the lancets are designed for single use and rapidly become blunt when used several times. Furthermore with the lancing devices and lancets of the prior art there is a risk that lancets will be inserted improperly into the lancing devices. Furthermore a user can be accidentally injured when the lancets and lancing devices are used improperly.

There have therefore been no lack of attempts to eliminate the said disadvantages. Lancing devices are known from U.S. Pat. No. 5,514,152, U.S. Pat. No. 5,152,775, U.S. Pat. No. 4,794,926 and U.S. Pat. No. 5,035,704 which store several lancets and can use these individually and in succession for lancing processes. After the lancing process the lancets can be removed individually from the device. Storage in a magazine and the ability to automatically dispense lancets helps to avoid mistakes when placing a lancet in a lancing device. In order to carry out the lancing movement, the lancet in the blood collection device (lancing device) must firstly be moved or deflected in a lancing direction (i.e. it's tip moves towards the body region to be pierced) and subsequently retracted as rapidly as possible into its initial position. In conventional lancet systems such as those described in EP-A 0 565 970 the part of the lancet that faces away from the tip is enclosed as tightly as possible by a lancet holder which is part of the lancing device and is moved in the lancing direction (forwards) as well as back to the starting position (backwards). The forwards and backwards movement is accomplished by a single drive mechanism which is often driven by a spring.

An automatic change of lancets by for example using a lancet magazine is difficult to realise with such a system in which it is necessary to enclose the lancet in a lancet holder. Moreover the lancet must have a lancet body which is adapted to the lancet holder and makes a firm connection between the lancet and holder especially to ensure the backwards movement. Consequently the lancets are often voluminous and their storage in a magazine would lead to large dimensions of the lancet system.

The lancet system described in U.S. Pat. No. 4,794,926 utilizes the elastic force of a leaf spring which is part of the lancet to move the lancet forwards and backwards. However, this propulsion method is unsuitable for essentially needle-like lancets.

A lancet system is known from U.S. Pat. No. 5,578,014 in which the drive of the lancet for the forwards movement operates independently of the drive for the return movement. The return movement is effected by a spring driven plunger which is part of the lancing device and acts on the lancet from behind i.e. on the end facing away from the tip. The return movement is driven by a spring which is incorporated in the lancet. Similar systems are described in U.S. Pat. No. 5,029,583 and DE-A 198 55 465. A disadvantage of this variant is that each lancet has to be equipped with its own spring which makes the manufacturing process complicated and expensive. Moreover it is very difficult to miniaturize the system.

Attempts to reduce the manufacturing costs for such lancets which are mass-produced articles (so-called disposables) often results in the obligatory use of cheap return springs. In this case the material properties are often subject to large variations which also means that there are also considerable variations in the return speeds. This can have a negative impact on the pain sensation during the lancing process.

The object of the invention is therefore to eliminate the disadvantages of the prior art. In particular it is an object of the present invention to provide a system for collecting blood or other body fluids which provides a plurality of lancets in the smallest possible space. This object is achieved by the subject matter of the invention.

SUMMARY OF THE INVENTION

The invention concerns a system for storing and providing lancets to collect a body fluid and in particular for blood collection. The invention also concerns a process for temporarily extending the tip of an essentially needle-shaped lancet from a system for storing and providing lancets to collect body fluids and in particular for blood collection. The invention also concerns a lancet magazine, a lancing device, and a lancet.

The system according to the invention comprises: i) a plurality of essentially needle-shaped lancets; ii) a drive unit which has a drive element such as a plunger which, in order to carry out a lancing process, is moved from a resting position into a lancing position; iii) a storage area to store the lancets; iv) a withdrawal area to guide at least the tip of the lancet out of the system during the lancing process and v) a transport unit which can transport lancets from the storage area into the withdrawal area. The drive element is arranged in the system according to the invention in such a manner that in the withdrawal area it can act on the lancet located there to carry out a lancing process for example by striking one end of the lancet like a hammer or a firing pin and thus moving the lancet from its resting position into a lancing position. In addition the system has a return device in the withdrawal area which can interact with the lancet located in the withdrawal area in order to move the lancet after completion of the lancing process from its lancing position into its resting position. In this process the drive unit and the return device act independently of one another on the lancet.

The system according to the invention comprises a plurality i.e. at least two essentially needle-shaped lancets. "Essentially needle-shaped" means that the lancets have a metal lancet needle with a tip which can be optionally ground. In this connection it is important that the lancet itself has no spring or such like which returns it to its initial position after the lancing movement. A central retraction device in the system returns the lancet.

A plastic lancet body made of an injection mouldable material can be injected onto the lancet needle in order to facilitate handling of the lancet in the system such as to transport the lancet from its storage position into the withdrawal position or to grip the lancet by the retraction device. The blunt end of the lancet needle i.e. the end facing away from the tip can also be compressed, flanged, bent or serrated to facilitate gripping of the lancet by the retraction device.

The lancet body is usually a plastic component which is mounted around the lancet needle and encloses it. The lancet body facilitates gripping of the lancet needle and can simply have a special shape adapted to the geometry of the lancing device. Hence the external shape of the lancet is essentially determined by the lancet body.

The tip of the lancet needle is preferably surrounded by a protective sheath in the unused state to ensure its sterility. This can be composed of the same material as the lancet body and then usually forms a single unit with this. The protective sheath can be separated from the lancet body and removed from the tip of the lancet needle before using the lancet. A predetermined breaking point is preferably located between the lancet body and protective sheath for this purpose.

The lancet of the invention comprises a needle (lancet needle) with a tip. The needle is usually several millimeters (mm) to a few centimeters (cm) in length and has an elongate shape. Needles typically have a cylindrical shape since this needle shape is particularly easy to manufacture; however, other needle shapes having different designs are also possible. The tip region of the needle comprises the needle tip which is inserted into the tissue when the lancet is used as directed. Hence the tip of the lancet needle is the part of the lancet which comes into contact with and may injure the skin of the individual to be pierced and thus causes a body fluid and in particular blood or interstitial liquid to flow out.

The tip of the lancet needle can for example be rotationally symmetrical as is generally the case for sewing needles. However, it has proven to be advantageous to provide the needle tip with one or several bevels. The edges formed in this manner which are slanted relative to the longitudinal axis of the needle and converge to form a tip act as a sharp cutting edge in the piercing process and make the piercing process less painful than is the case with rotationally symmetrical needles. The lancet needle of the lancet according to the invention is manufactured from a material which is hard enough to withstand mechanical stress without deformation during the piercing process, during the processing steps for its manufacture or other stresses which may occur. In addition the material must be such that no particles break off or become detached during the piercing process. Finally it must be possible to machine the needle in such a manner that the needle tip is sufficiently pointed and the edges of the needle tip can optionally be ground to a sufficient sharpness. Materials that are very suitable for the lancet needle are above all metals and of these especially high-grade steels. However, needles made of ceramics, silicon or plastics are also conceivable. High-grade steel needles are particularly preferred.

In a preferred embodiment at least the tip of the lancet needle of the lancet according to the invention is surrounded by a plastic body which is referred to in the following as the lancet body. In this connection it is preferable that the lancet body is made of an elastic material in the area of the tip of the lancet needle. At least the tip of the lancet needle is completely surrounded on all sides by this elastic material i.e. it is embedded in it and thus sealed from the surroundings. The elastic material of the lancet body which in various embodiments can completely or only partially form the lancet body is characterized in that it is soft, deformable and can be pierced by the tip of the lancet needle without damaging the tip. In the lancing process the lancet needle is moved along its longitudinal axis relative to the lancet body and its tip emerges from the lancet body in order to thus be able to pierce the skin of the individual to be examined in order to collect blood. Another important property is that the elastic material again closes around the tip of the lancet needle when the lancet needle is retracted into the lancet body. After the lancing process the lancet needle can be returned to its initial position relative to the lancet body by reversing the piercing movement in a preferred embodiment and in this position the tip is again completely enclosed on all sides by the elastic material of the lancet body.

The elastic material of the lancet body which completely encloses the tip of the lancet needle ensures the sterility of the lancet needle tip before use and preferably until immediately before use and optionally encloses the lancet needle tip after use. Consequently the elastic material is impenetrable to germs. In addition the elastic material represents a mechanical protection for the lancet needle tip and thus also prevents unintentional injury on the lancet needle tip.

Suitable elastic materials for the lancet body of the present embodiment have proven to be rubber, caoutchouc, silicons, elastomers and in particular thermoplastic elastomers. These have important properties for the present invention: they are soft, deformable, can be pierced by the lancet needle without damaging the tip and they form a tight seal around the used lancet needle tip. Furthermore they can be used for injection moulding processes which enables the lancets to be mass-produced in large numbers.

During the piercing process the lancet needle is moved relative to the lancet body. In this process the latter is preferably fixed in its position by the lancing device or the lancing instrument. The lancet needle can contain suitable elements for the purpose of driving it in a forward and/or backward direction. In particular it can have a special shape such as a needle head, a flange, a bend or a recess at the end opposite to the tip, or it can have an additional lancet body which is engaged by the drive element of the lancet system in addition to the lancet body which encloses the tip.

The form of the needle or of the additional lancet body can interact in a suitable manner with a corresponding drive device and/or retraction device in the lancing apparatus (lancing device).

In order to increase the stability of the elastic material it is possible to combine it with a stiff material such as a stiff plastic material. In this case the outside of the elastic material which does not come into contact with the lancet needle can for example be stabilized with a layer of a stiff material such as a stiff plastic. It is also possible to manufacture only the lancet needle tip region of the lancet body from an elastic material and to use a conventional stiff plastic in the other regions of the lancet body. In this connection the elastic material and the stiff material can be glued together or joined together in an injection moulding process for example in a two-component injection moulding process. The stiff material of the lancet body mechanically stabilizes the elastic material during the lancing process and simplifies the fixing of the elastic part of the lancet body in the lancet system during the lancing process.

In a further preferred embodiment the lancet contains a lancet needle comprising a tip and a hollow body which surrounds at least the tip of the lancet needle, the tip region of the lancet needle being movable in the hollow body and the hollow body being sealed by a foil that can be pierced by the tip of the lancet needle during the lancing process and can optionally reseal after the tip of the lancet needle has been retracted into the hollow body.

The regions of this hollow body which do not come into contact with the lancet material are preferably manufactured from a stiff, preferably injection mouldable material.

During the lancing process the lancet needle is moved relative to the hollow body which represents the lancet body. The holder and drive for the lancet needle and the attachment of the lancet body can be realised as described above by suitable constructional measures.

The elastic material which comprises a part of the hollow lancet body is pierced by the lancet needle tip during the lancing process and optionally reseals after the lancet needle tip has been retracted again into the hollow body and thus seals the hollow body. Hence the lancet needle tip is sealed in a sterile manner in the hollow body until immediately before use and is hygienically enclosed in it after use.

The lancet of this embodiment can in addition to the lancet body which encloses the tip of the lancet needle have a further lancet body which interacts with suitable elements of a lancing device during the lancing process. In addition the lancet needle can have a special shape; for example it can have a head at the end opposite to the tip to facilitate the propulsion of the lancet.

In a preferred embodiment the essentially needle-shaped lancet has a pinhead at the end opposite to the tip. In the system according to the invention this can interact with the retraction device such that the retraction device can move the lancet back into the starting position (resting position) after the lancing process. The pinhead can, as is for example the case with pins, be an integral part of the lancet needle. The lancet needle is then preferably manufactured from one piece in particular from one metal. However, it is also possible that the pinhead is a separate part connected to the needle such as a plastic part injected onto the needle. The pinhead can be a flattened end of the lancet needle provided with a bead, such as the head of a pin or the striking surface of a nail. Alternatively the pinhead can be a terminal thickening of the lancet needle or a ring surrounding the lancet needle and sealing tightly against it or a disk placed on the blunt end of the needle.

The system according to the invention also contains a drive unit for the lancet. The drive unit contains a drive element such as a plunger or a hammer which is moved from a resting position into a lancing position in order to carry out a lancing process. The drive element is arranged in the system according to the invention in such a manner that in the withdrawal area it can act on the lancet located there to carry out a lancing process for example by striking one end of the lancet like a hammer or a firing pin and thus moving the lancet from its resting position into a lancing position. In connection with the present invention it is important that although the drive unit causes the forward movement of the lancet i.e. the movement which brings the lancet from its resting position into the lancing position, it does not cause the reverse movement of the lancet. The drive unit can be designed in a known manner and for example be equipped with a spring drive and optionally gear elements. Such drive elements are in principle known to a person skilled in the art and can be easily realised.

Many embodiments of suitable drives are known from the prior art. The drive plunger executes a push movement and subsequently a retraction movement. During the push movement the lancet is also moved forwards i.e. in its lancing direction. During the retraction movement of the drive element it no longer acts on the lancet. This allows the lancet to also move backwards. Since the lancet is coupled to a retraction device according to the invention this can also take over the return movement of the drive plunger. This is for example appropriate when the drive is a simple cam like those known from the valve drives of engines. This is also the case for simple spring-loaded plungers which are propelled forwards from the tensioned position and strike the lancet and hence move it forwards. In contrast in the case of a constrained control of the movement of the drive element i.e. when the forward as well as the return movement of the drive element is achieved by a suitable drive, the return unit only moves the lancet.

The system according to the invention is used especially to store and to automatically provide lancets for lancing processes and to carry out lancing processes. It therefore also has a storage area to store the lancets. For example the system can have a space for holding a lancet magazine. At least the unused lancets can be accommodated in the storage area. However, it is preferably also possible to store the used lancets until their disposal. The system can also have separate storage areas for unused and used lancets.

In addition the system of the present invention has a withdrawal area for guiding at least the tip of a lancet out of the system during the lancing process. In order to carry out a lancing movement a lancet located in the system is firstly transported from the storage area into the withdrawal area. Here the lancet is then in a position which can, on the one hand, be driven by the drive element of the drive unit in a forward direction i.e. in the direction of the lancing movement and in which it can, on the other hand, interact with the retraction device in a suitable manner in order that it can be brought back into its starting position after the lancing process. Suitable constructional measures should ensure that the lancet in the withdrawal area can interact in particular with the drive element as well as with the retraction device. Furthermore the system according to the invention has an opening in the withdrawal area which enables the lancet tip to protrude from the system during the lancing process.

A further component of the system according to the invention is a transport unit which can transport lancets from the storage area into the withdrawal area. The transport unit can be driven and/or controlled manually or automatically. The exact type of transport unit is not important for the present invention and can vary depending on the exact manner of storage of the lancets in the system. The transport unit can be driven manually or with the aid of a spring or motor.

In addition the system has a central retraction device in the withdrawal area which can interact with the lancet located in the withdrawal area in order to move the lancet from the lancing position into its resting position after the lancing process has been carried out. The drive unit and the retraction device act independently on the lancet. The retraction device has a spring mechanism in a preferred embodiment which particularly preferably comprises a leaf or spiral spring. Alternatively the retraction device can contain a deformable elastomer for example a compressible rubber block which relaxes when it is unloaded and thus causes the return movement. Particularly preferred embodiments of the retraction device as well as their special interaction with the lancets are described in conjunction with the figures (see below). In contrast to the state of the art the system according to the invention only has a central retraction device which means that individual lancets do not have a return spring or such like to move them back into the starting position after the lancing movement has been carried out.

It will be apparent that the lancets, drive unit and return device of the system according to the invention have to be mutually compatible. For example the form of the lancet can fit that of the retraction device at least in the return direction. This can be achieved by shaping the lancet like a sliding block in a machine tool which engages in a corresponding T slot or a simple slot in sheet metal (cf. for example FIGS. 1A and 1B, further below). In order to transport the lancet further the drive mechanism can also be disengaged which enables the return mechanism to be designed as a spring-loaded fork that simply engages behind the thickened end of the lancet (see FIG. 3, further below). The slot in the return spring designed as a leaf spring can also be conically narrowed in the inlet of the lancet and become wider again in the outlet so that the lancet is only a smooth needle the middle of which, i.e. the constriction, is pinched on one side and is thus docked on to the return spring. The blunt plunger of the drive then moves the needle forwards, the spring returns it again when the plunger has retracted.

The lancets of the system according to the invention are preferably accommodated in a lancet magazine. This can be removed from the system after the lancets have been consumed and replaced by a new magazine. In this manner the user of the system can replace the used lancets by new ones in a simple manner.

The lancet magazine preferably also contains the retraction device for the lancets. This is especially advantageous when the retraction device has a spring mechanism: With each change of magazine the system is provided with a new unused drive spring for the return mechanism. Hence it is possible to largely avoid fatigue phenomena of the spring material. This enables the movement to be kept constant which in turn reduces pain during lancing. In addition in such an embodiment no interface is necessary between the retraction device and the instrument which holds the lancet magazine. The magazine and thus also the entire system containing the magazine can thus be constructed in a very compact manner.

The magazine according to the invention for lancets contains in addition to a plurality of essentially needle-shaped lancets, among others a storage area to store the lancets and a withdrawal area to extend at least the tip of a lancet from the magazine during the lancing process. In the withdrawal area of the magazine there is either a retraction device that can interact with the lancet that is located in the withdrawal area in order to move the lancet from the lancing position into its resting position after carrying out the lancing process or it allows engagement of a retraction device, which is for example contained in the lancing device. Details of the individual components of the lancet magazine essentially correspond to the statements made above in connection with the system according to the invention.

A preferred embodiment of the lancet magazine additionally contains a transport unit which can transport the lancets from the storage area into the withdrawal area. The transport device can preferably interact with an appropriate drive unit in a blood collection instrument (also referred to in the short form as lancing device) when the magazine is present in such an instrument. In this case the magazine can contain part of the drive gear for the transport unit whereas a drive motor for the transport unit is for example located in the blood collection instrument. Moreover it is also possible that the transport unit and in particular its drive motor and its gears are located completely in the magazine and only its control and optionally energy supply are outside the magazine.

An additional subject matter of the invention is a lancing device which is suitable for use in a system for storing and providing lancets to collect body fluids and in particular for blood collection as described above. Like the system according to the invention the lancing device comprises a drive unit which has a drive element (for example a hammer or a plunger) which is moved from a resting position into a lancing position in order to carry out a lancing process. In addition the lancing device has a storage area to store lancets and a withdrawal area to extend at least the tip of the lancet from the system during the lancing process. In addition the lancing device contains a transport unit which can transport lancets from the storage area into a withdrawal area. The drive element is arranged such that it can act in the withdrawal area on the lancet located there in order to carry out the lancing process and thus move it from a resting position into a lancing position. In one embodiment the lancing device has a retraction device in the withdrawal area that can interact with the lancet located in the withdrawal area in order to move the lancet from the lancing position into its resting position after carrying out the lancing process. Alternatively the lancing device can hold a lancet magazine described above in more detail which in turn contains a retraction device. The individual elements of the lancing device essentially correspond to the elements described above of the system according to the invention.

The process according to the invention is used to temporarily move the tip of an essentially needle-shaped lancet out of a system for storing and providing lancets in order to collect body fluids and in particular for blood collection. It is especially suitable for the system according to the invention described above. In the process according to the invention a drive element such as a plunger is moved from its resting position towards its lancing position. It thereby propels a lancet from its resting position until it reaches its lancing position. After the lancet has reached its lancing position it is returned to its resting position with the aid of a retraction device. The forwards movement of the lancet i.e. the movement from the resting position into the lancing position is thus effected by the drive unit and in particular the drive element; the return movement is effected by a separate retraction device that is independent of the drive unit. In this connection the retraction device can in addition to the lancet also return the drive element to its resting position.

BRIEF DESCRIPTION OF THE DRAWINGS

The invention is further elucidated by the following FIGS. 1 to 11.

FIG. 1 shows a schematic detail of a system according to the invention for a preferred embodiment in which the interaction between the drive element, lancet and retraction device before the lancing movement (FIG. 1A) and at the end of the lancing movement (FIG. 1B) are shown.

FIG. 2 shows schematically for a preferred embodiment a perspective, partially cut-out view into a lancet magazine of the system (FIG. 2A) and a corresponding top-view in which the cover of the magazine housing has been removed (FIG. 2B).

FIG. 4 shows schematically for a further preferred embodiment a detail of the system according to the invention in which the interaction between the drive element, lancet and retraction device before the lancing movement (FIG. 4A) and at the end of the lancing movement (FIG. 4B) are shown.

FIG. 5 shows schematically for a further preferred embodiment a detail of the system according to the invention in which the interaction between the drive element, lancet and retraction device before the lancing movement (FIG. 5A) and at the end of the lancing movement (FIG. 5B) are shown.

FIG. 6 shows schematically for a further preferred embodiment a detail of the system according to the invention in which the interaction between the drive element, lancet and retraction device before the lancing movement (FIG. 6A) and at the end of the lancing movement (FIG. 6B) are shown.

FIG. 9 shows a schematic detail of the system according to the invention for a preferred embodiment in which the interaction between the drive element, lancet and retraction device before the lancing movement (FIG. 9A) and at the end of the lancing movement (FIG. 9B) are shown.

FIG. 10 shows a schematic detail for another preferred embodiment which can be regarded as a variant of the embodiment shown in FIG. 9 of the system according to the invention in which the interaction between the drive element, lancet and retraction device before the lancing movement (FIG. 10A) and at the end of the lancing movement (FIG. 10B) are shown.

FIG. 11 shows a schematic detail for another preferred embodiment which can be regarded as a variant of the embodiment shown in FIG. 9 of the system according to the invention in which the interaction between the drive element, lancet and retraction device before the lancing movement (FIG. 11A) and at the end of the lancing movement (FIG. 11B) are shown.

Brief Description of Components
The numbers and letters in the figures denote:

| | |
|---|---|
| 1 | lancet |
| 2 | lancet needle |
| 3 | lancet body |
| 4 | lancet head |
| 5 | lancet needle tip |
| 6 | drive element |
| 7 | retraction device |
| 8 | leaf spring |
| 9 | slit |
| 10 | lancet magazine |
| 11 | housing |
| 12 | guide channel |
| 13 | opening |
| 14 | stationary part of the retraction device 7 |
| 15 | movable part of the retraction device 7 |
| 16 | spiral spring |
| 17 | push rod |
| 18 | transport device |
| 19 | tilt axis |
| 20 | cam |
| 21 | recess in lancet body 3 |
| 22 | cross-pieces of the lancet body 3 |
| 23 | stop for the lancet body 3 |
| 24 | recess |
| 25 | guide element of the drive element 6 |
| 26 | guide element |
| A | direction of movement of the drive element 6 |
| B | direction of movement of the push rod 17 |
| C | direction of movement of the retraction device 7 when it is tilted about axis 19 |
| D | direction of movement of the transport device 18 |

DESCRIPTION OF THE PREFERRED EMBODIMENTS

FIG. 1 shows a schematic detail of a preferred embodiment of the system according to the invention. FIG. 1 mainly serves to illustrate the interaction between the lancet (1), the drive element (6) of the drive unit and the retraction device (7). Of the five lancets (1) shown in FIG. 1 the second lancet from the left is directly above the drive element (6). This position marks the withdrawal area of the system according to the invention. In this position the lancet (1) located there can be propelled by the drive element (6) to execute the lancing movement. At the same time the lancet (1) located in the withdrawal area is within the slit-shaped recess (9) of the leaf spring (8) which is part of the retraction device (7). In addition to the lancet needle (2), the lancet (1) contains a lancet body (3) which before use envelops the tip of the lancet needle (2). The lancet (1) has a lancet head (4) at the end of the lancet needle (2) opposite to the tip (5). This head and the lancet body (3) can be injected around the lancet needle (2) in an injection moulding process and are preferably composed of an injection mouldable plastic. The lancet body (3) is preferably made of an elastic material whereas the lancet head (4) is composed of a rigid material, However, it is also possible to mould both components of the lancet (1) from a rigid material.

Figure 1A:
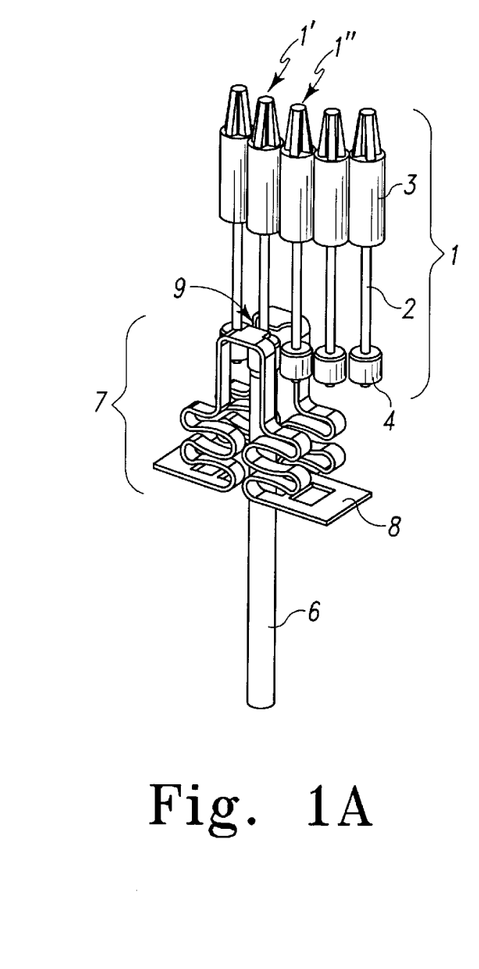

In FIG. 1A the lancet (1') located in the withdrawal area is in its resting position. Hence FIG. 1A represents the state of the system before or after carrying out a lancing movement.

Figure 1B:
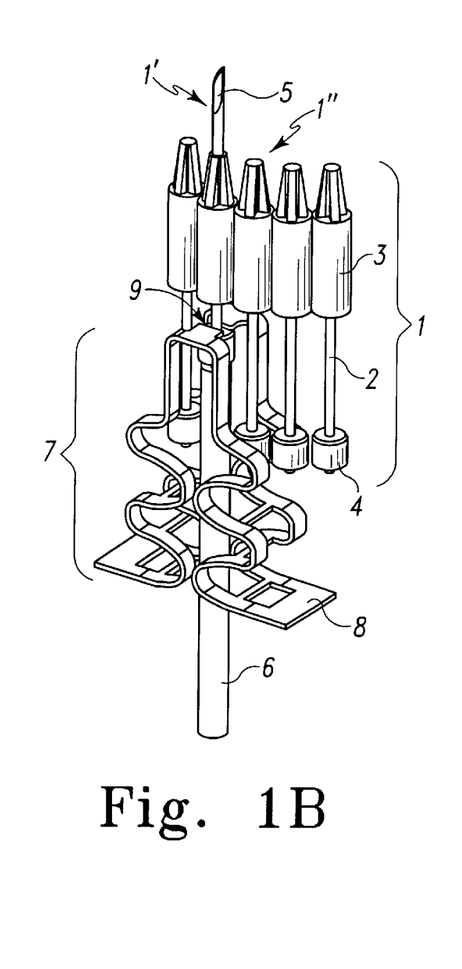

In FIG. 1B the lancet (1') located in the withdrawal area is in the lancing position. The needle tip (5) is moved out of the lancet body (3). The drive element (6) acts on the end of the lancet needle (5) opposite to the lancet needle tip (2). The lancet head (4) interacts with the leaf spring (8) of the retraction device (7) and stretches it from its resting position. The slit (9) of the leaf spring (8) is wide enough to receive the lancet needle (2). On the other hand it is narrow enough to offer a surface for interaction with the lancet head (4).

As soon as the drive element (6) no longer exerts force on the lancet (1'), the leaf spring (8) of the retraction device (7) ensures that the lancet (1') located in the withdrawal area is returned to its resting position. The position of the lancet body (3) is fixed during the lancing movement. This can either be achieved in that the individual lancet bodies (3) of the various lancets (1) are directly connected to one another for example via common cross-pieces or in that the lancet body (3) is attached to a stiff tape-shaped material which is not shown here in the figures. Alternatively it can be fixed by means of the magazine or its housing.

After the lancing movement has been carried out and the lancet needle (2) has been returned to its resting position, the spent lancet (1') is transported from the withdrawal area into the storage area. During this the next lancet (1") moves simultaneously from the storage area into the withdrawal area.

Figures 2A, 2B:
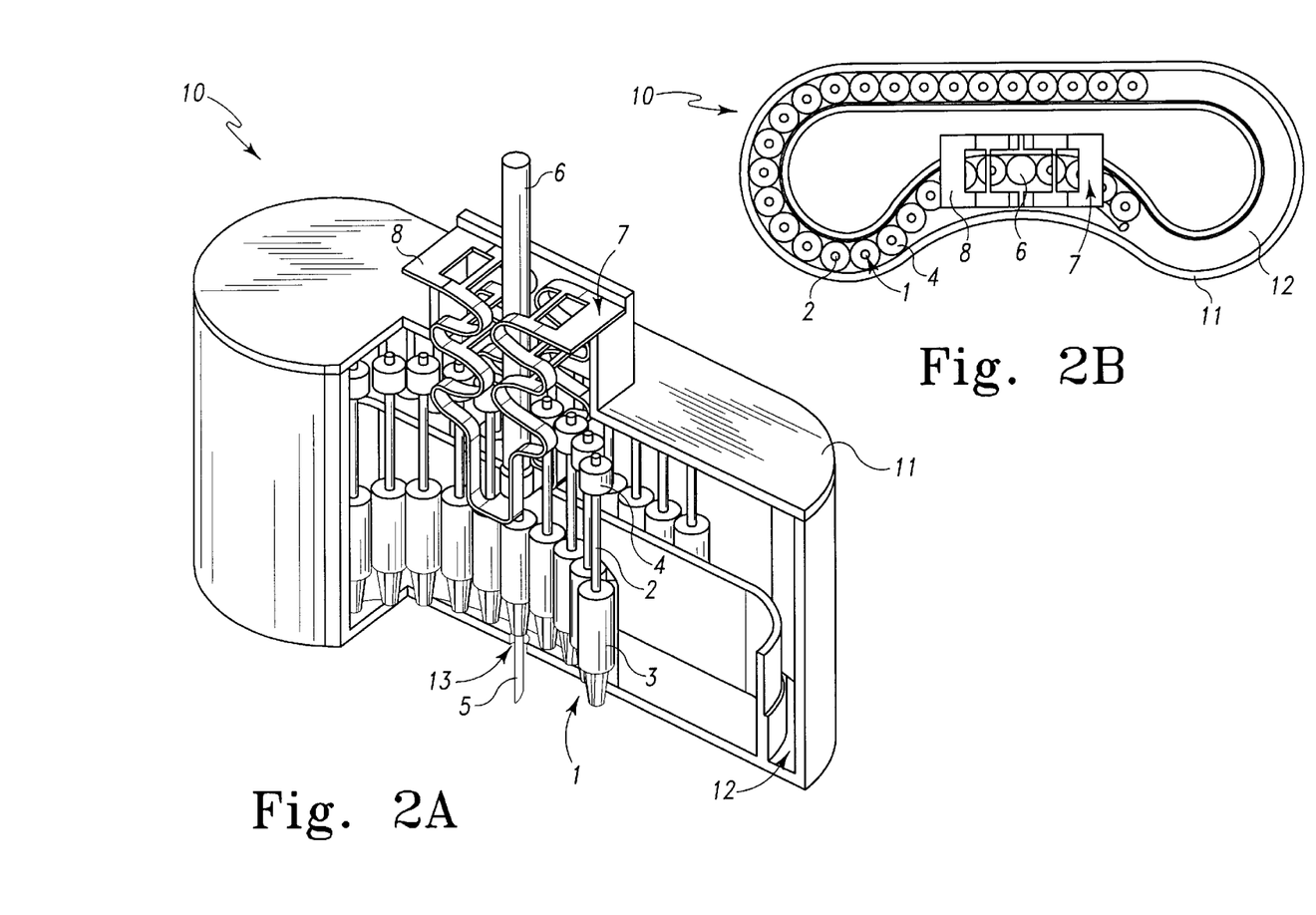

FIG. 2 shows a possible embodiment of the components of the system according to the invention described in FIG. 1. FIG. 2A shows a lancet magazine (10) in a perspective partially cut-out view of a lancet magazine in which the elements of the inventive system shown in FIG. 1 are integrated. FIG. 2B shows the same magazine (10) in a schematic top-view in which the upper cover of the lancet magazine housing (11) has been removed to give a view of the interior of the magazine (10). In FIG. 2A the system is shown in the state already shown in FIG. 1B.

The drive element (6) of the drive unit presses from above onto the lancet needle (2) of the lancet (1) which is located in the withdrawal area. The lancet needle tip (5) is pushed out of the lancet body (3) and the leaf spring (8) of the retraction device (7) is in a stretched state. The magazine (10) has an opening (13) in its housing (11) from which the lancet needle tip (5) can emerge to carry out the lancing process.

As shown especially in FIG. 2B the connected lancets (1) are moved in a guide channel (12) of the housing (11) of the magazine (10) from the storage area into the withdrawal area and after completion of the lancing movement back into the storage area. The individual lancets (1) are safely shielded from the environment by the housing (11) of the magazine (10) before and also after the lancing process.

Since the lancets (1) can be substantially miniaturized, a large number of them can be accommodated in a very small space. Integration of the retraction device (7) in the lancet magazine (10) ensures that the leaf spring (8) of the retraction device (7) is renewed with each change of magazine and thus prevents fatigue of the material of the retraction device (7). In addition the magazine makes it simple and safe to couple the lancing device and lancets.

Figure 3:
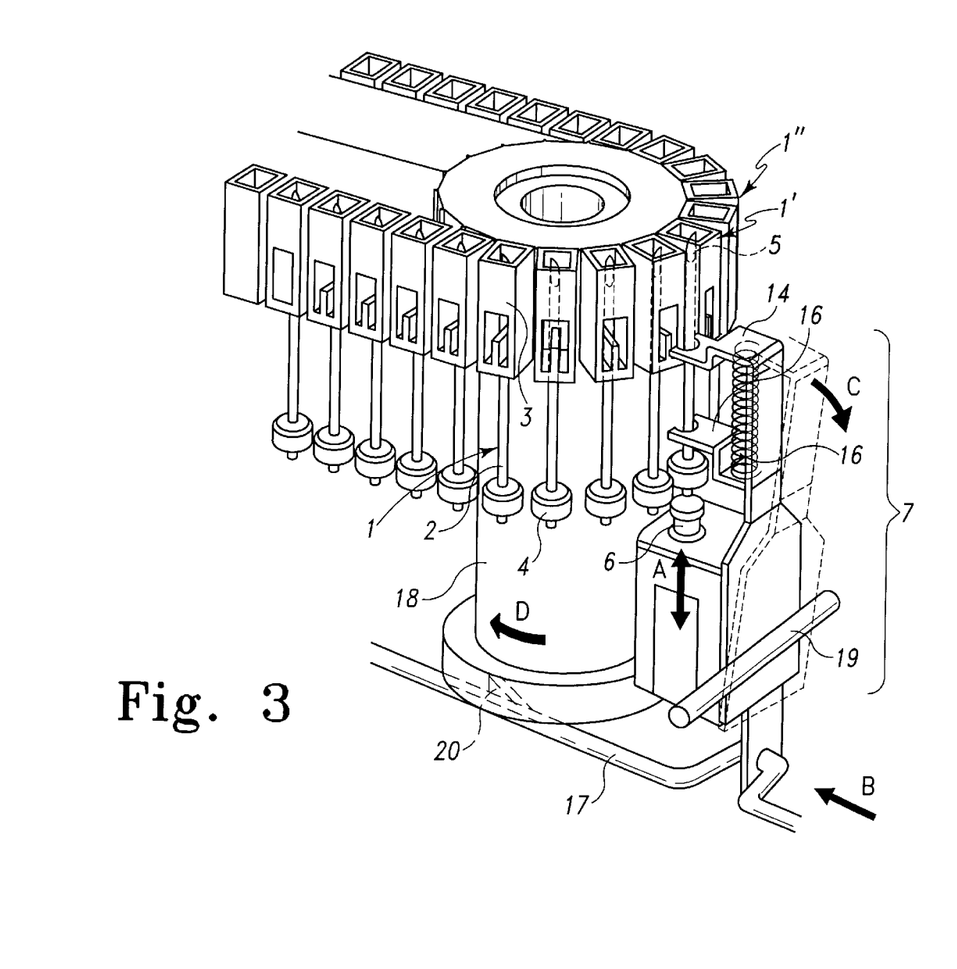
FIG. 3 shows schematically a further alternative embodiment of the system according to the invention.

Another alternative embodiment of the system according to the invention is shown in FIG. 3. FIG. 3 essentially shows a plurality of essentially needle-shaped lancets (1), a drive device with the drive element (6), a retraction device (7) and a transport device (18).

The individual lancets (1) are connected together in the area of the lancet body (3). In the case shown the lancet body (3) is mounted on a conveyor belt. However, another possibility is for the individual lancet bodies (3) to be connected together via their contiguous edges by means of joints or film hinges.

Like the lancets of FIG. 1 and FIG. 2, the lancets (1) of FIG. 3 have a lancet needle (2) with a lancet needle tip (5) which in the resting state is enclosed in the lancet body (3). In order to ensure the sterility of the lancet needle tip (5) before use, the top of the lancet body (3) can be sealed with an elastic material that can be pierced by the lancet needle tip (5) (not shown). The lancet head (4) is located at the end of the lancet needle (2) opposite to the tip. The lancet head (4) and the lancet body (3) are preferably injected from an injection mouldable material onto the lancet needle (2). They can be composed of the same material or of different materials.

One of the lancets (1) shown in FIG. 3 is located directly above the drive element (6) and is thus in the withdrawal area. The other lancets are in the storage area.

In the withdrawal area the retraction device (7) acts on the lancet (1') located there. In the present case the return device (7) has an essentially stationary part (14) and a movable part (15). Both parts have an essentially semicircular recess which can partially enclose the lancet needle (2) of the lancet (1') in the withdrawal area.

If the drive element (6) is moved upwards in direction A in order to drive the lancet (1') located in the withdrawal position out of its resting position for lancing, the lancet head (4) strikes the movable part (15) of the return device (7). When the lancing movement is executed the movable part (15) is pushed against the stationary part (14) and as a result the spiral spring (16) is compressed. After the lancing movement has been carried out the drive element (6) is retracted in direction A downwards into its starting position. The compressed spiral spring (16) of the retraction device (7) now relaxes and in so doing presses the movable part (15) downwards. In this process the movable part (15) presses downwards on the lancet head (4) and thus guides the lancet (1') from its lancing position into its resting position.

Afterwards the spent lancet (1') can be transported from the withdrawal area into the storage area. At the same time another lancet—in the present case the lancet (1") on the right next to the used lancet (1')—is transported from the storage area into the withdrawal area. For this the push rod (17) is moved in direction B. This movement tilts the return device (7) about the axis (19) in direction C (this state is indicated by the dashed lines). As a result of this tilting movement the lancet (1') located in the withdrawal area is released by the return device (7) i.e. parts 14 and 15 are pulled back from the lancet needle (2). At the same time the movement of the push rod (17) in direction B turns the transport device (18) in direction D. Transfer of the movement of the push rod (17) to the transport device (18) can for example be achieved by a bevelled cam (20). Movement of the transport device in direction D conveys the next lancet (1") from the storage area into the withdrawal area and at the same time transfers the spent lancet (1') from the withdrawal area into the storage area. As a result of the return movement of the push rod (17) into its starting position the retraction device (7) is also tilted back and can thus act on the next lancet (1) to be used.

Figures 4A, 4B:
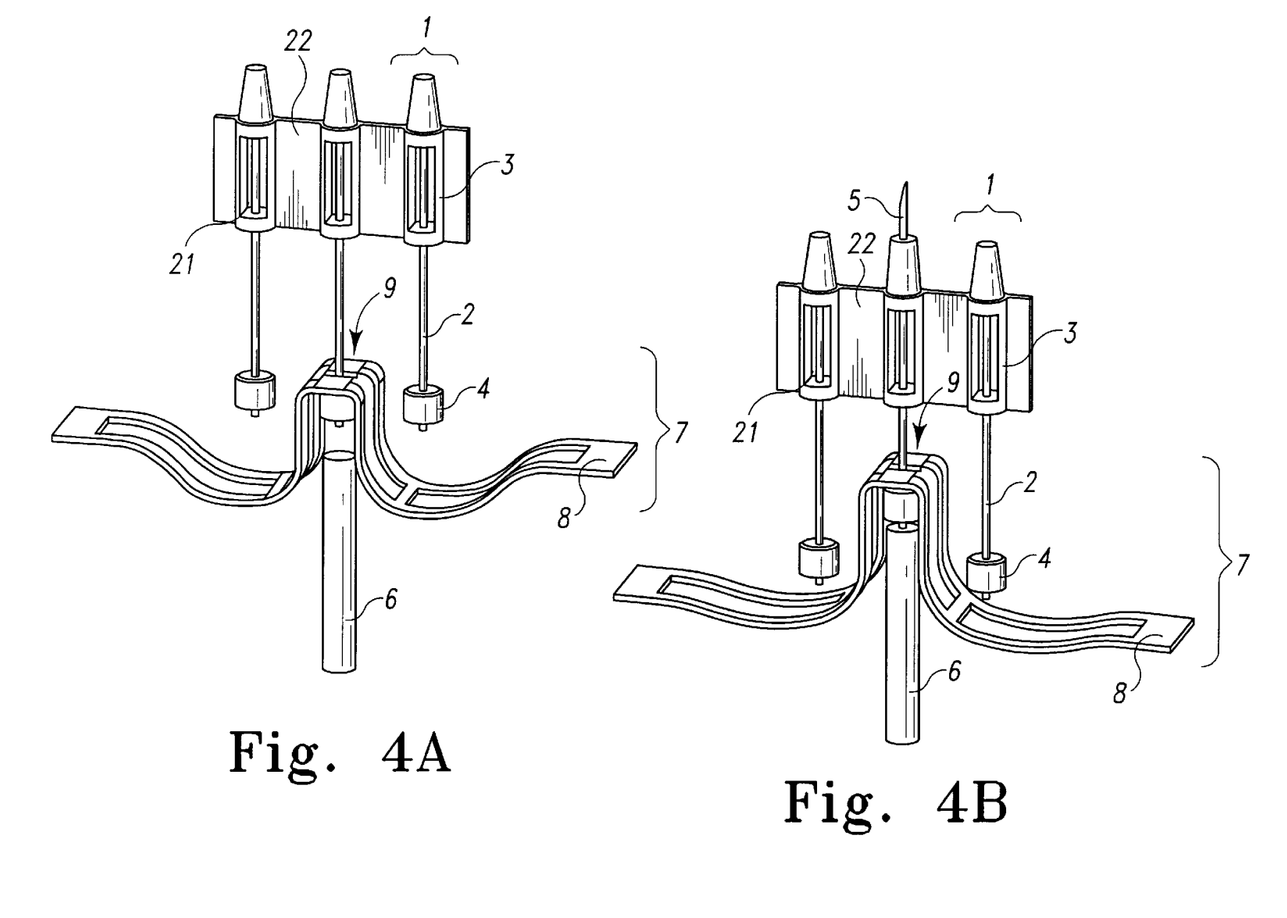

FIG. 4 shows schematically a variant of the system according to the invention from FIG. 1. In this variant the leaf spring (8) of the retraction device (7) has a different shape whereby this shape with a more simple design has similar functionality to the shape shown in FIG. 1. The detailed drawing 4A shows the situation before and after the lancing process; detailed drawing 4B shows the situation with the lancet (1) in the lancing position.

In contrast to the embodiment of FIG. 1 the individual lancets (1) are in this case further apart. The lancet bodies (3) are connected by means of cross-pieces (22) which can fix or support the lancets (1) during the lancing process.

The lancet (1) in this embodiment contains a lancet body (3) which encloses the shaft of the lancet needle (2) at two positions. In alternative embodiments several positions of the lancet needle (2) can of course also be enclosed. The blunt end of the needle (2) can have an injected lancet head (4) or an equivalent element which serves to couple it to the return device (7). The needle tip (5) is embedded in the plastic of the lancet body (3) in order to ensure the sterility of the needle tip (5) until use. Alternatively the lancet needle tip (5) can be stored sealed in a hollow space one side of which is sealed by a foil (cf. FIG. 3).

The lancet (1) is constructed such that when the lancet body (3) is fixed (by the lancet magazine (10) or instrument) the lancet needle (2) in the lancet body (3) can move in the lancing direction. Pushing the lancet needle (2) out of the plastic of the lancet body (3) is facilitated by keeping the needle shaft as smooth as possible by for example polishing the positions that have been moulded in. In addition the lancet needle (2) can be provided with a suitable lubricant in the area of the sheathing in order to improve gliding of the lancet needle through the plastic of the lancet body (3).

The enclosure of the shaft of the lancet needle (2) in at least two positions along the needle shaft enables an exact axial positioning of the lancet needle (2). The enclosure of the needle shaft is achieved in such a manner that only a, 5 very small surfaces of the lancet needle (2) are moulded in by the plastic of the lancet body (3) in order to achieve the lowest possible frictional resistance (if possible less than 1 N). The dimensional stability of the selected plastic should be such that it is not deformed when the lancing movement is carried out. Polyethylene or polypropylene have for example proven to be suitable. As a consequence of the dimensional stability of the lancet body (3) and the embedding of the lancet needle (2) at least two points, the lancet needle (2) can be guided largely free of play and cannot swing from side to side when the lancet body (3) is fixed. This can reduce the pain caused by the lancing.

The drive element (6) moves the lancet needle (2) in the piercing direction through the lancet body (3). In this process the lancet needle (2) is not laterally guided by the drive element (6). The lateral guidance is achieved by the lancet body (3) or by the composite structure of the individual lancet bodies (3).

In the case of the lancet shape shown in FIG. 4 it has proven to be advantageous to select a material for the lancet body (3) which at the same time serves as a hermetic seal which is so soft (having a shore hardness A of 30 and less) that the lancet needle tip (5) is not deflected too strongly sideways during the lancing movement as a result of its asymmetric bevel and that the frictional forces during lancing are as low as possible (if possible less than 1 N).

When moulding the lancet needle tip (5) into the plastic of the lancet body (3), the geometry (shape) and the wall strength of the moulding of the lancet needle tip (5) should be designed such that the lancet needle tip (5) can easily pierce the plastic and the frictional forces during lancing are as low as possible (if possible less than 2 N).

Figure 5A:
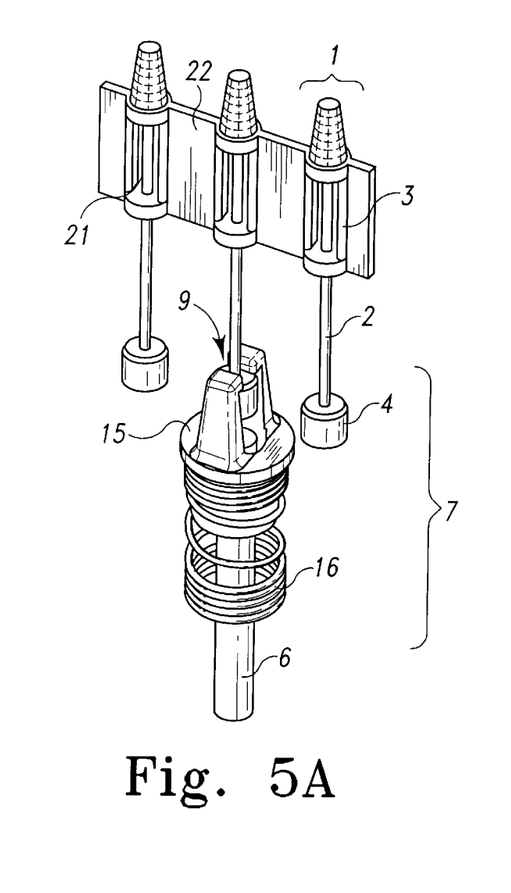
Figure 5B:
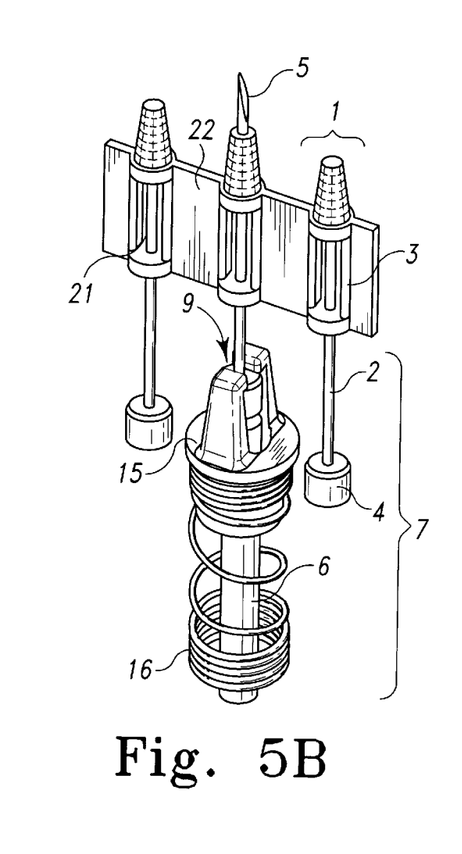

FIG. 5 shows schematically a further alternative embodiment to those shown in FIGS. 1 and 4 of the system according to the invention. The detailed drawing 5A shows the situation before and after the lancing process; the detailed drawing 5B shows the situation with the lancet (1) in the lancing position.

The lancet (1) or the unit of lancets in FIG. 5 essentially corresponds to the embodiment of FIG. 4. In the embodiment shown here the retraction device (7) contains a movable part (15) which has a gripping device with a slit (9) to receive the lancet (1). The movable part (15) is connected via a draw-in bolt spring (16) to a stationary part (not shown) of the retraction device (7). During the phase of the lancing movement during which the drive element (6) acts on the lancet (1) the spring (16) is stretched since the head (4) of the lancet (1) is connected to the movable part (15) of the retraction device. As soon as the transfer of force by the drive element (6) is completed i.e. as soon as the lancet needle tip (5) has been completely driven out for the lancing, the tension spring (16) can return to its relaxed original position. In this process it takes the lancet needle (2) back into the starting position and optionally also transports the drive element (6) into its starting position.

Figure 6A:
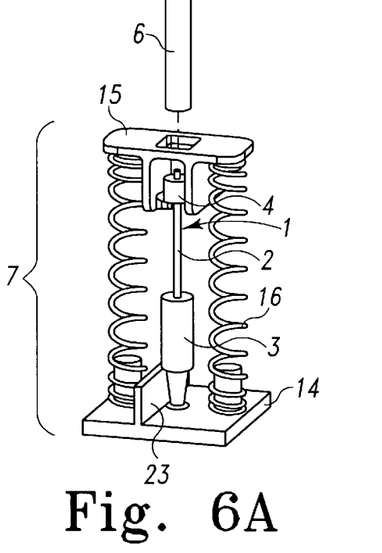
Figure 6B:
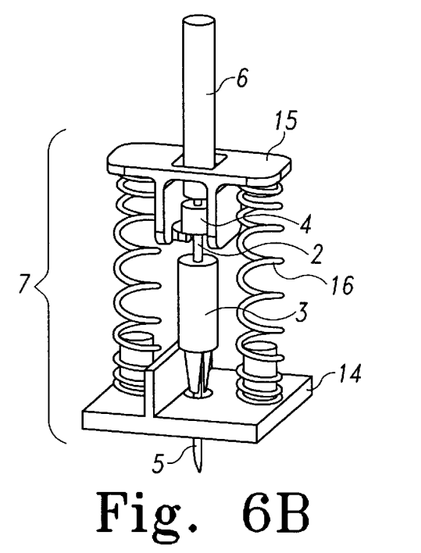

FIG. 6 also shows a schematic diagram of an alternative embodiment of the system according to the invention. Lancet (1) in this case essentially corresponds to the embodiment of FIG. 1. The detailed drawing 6A shows the situation before and after the lancing process; the detailed drawing 6B shows the situation with the lancet (1) in the lancing position i.e. with an extended lancet needle tip (5).

Like in FIG. 5 the retraction device in this case is formed from two parts (14,15) that can move relative to one another, one of which (14) is stationary and the other (15) interacts with the lancet (1) during the lancing movement by enclosing the head (4) of the lancet (I) and moving with the lancet (1). The stationary part (14) contains a cut-out (hole) through which the lancet needle tip (5) can pass. In contrast to FIG. 5 the retraction device (7) in FIG. 6 additionally has a pressure bolt spring (16) which is compressed when the lancing movement is carried out. As soon as the transfer of force by the drive element (6) is completed i.e. as soon as the lancet needle tip (5) has been completely driven out for the lancing, the tension spring (16) can return to its relaxed original position. In this process it takes the lancet needle (2) back into the starting position and optionally also transports the drive element (6) into its starting position.

The embodiment shown in FIG. 6 contains a stop (23) for the lancet body (3) on the side of the stationary part (14) of the return device (7) which faces the lancet (1) which prevents the lancet body (3) from moving with the lancet needle (2) during the lancing movement. This ensures that the tip (5) of the lancet needle (2) can move out from the body (3) and thus be available for the lancing process.

Figure 7:
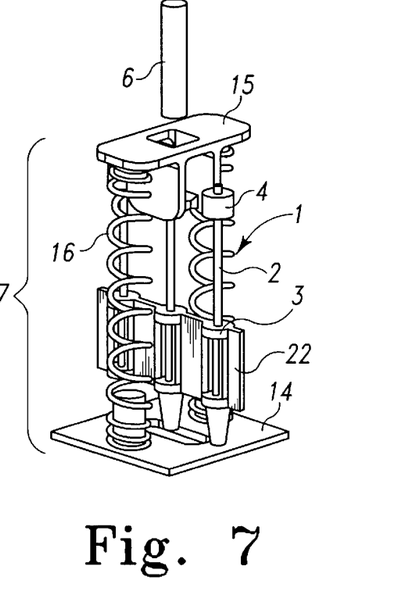
FIG. 7 shows schematically a variant of the system from FIG. 6 in which only the situation before the lancing movement is illustrated.
Figure 8:
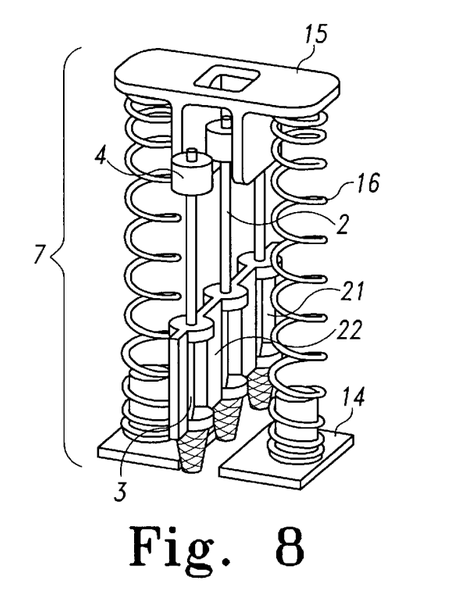
FIG. 8 shows a further variant of the system of FIG. 6 in which in this case only the situation before the lancing movement is shown.

The embodiments of the system according to the invention shown in FIGS. 7 and 8 are variants of the embodiment of FIG. 6. FIG. 7 as well as FIG. 8 only show the starting position of the system. In both figures the lancets (1) or the corresponding lancet combinations composed of several lancets correspond to those of FIGS. 4 and 5. Since the lancets (1) in this case are connected together by cross-pieces (22) which fix the lancet bodies (3) relative to one another, a stop (23) is unnecessary. The stationary parts (14) of the return device (7) have alternative recesses in FIGS. 7 and 8 compared to the embodiment of FIG. 6 (longitudinal slit in FIG. 7; parts separated by a gap in FIG. 8).

Figure 9A:
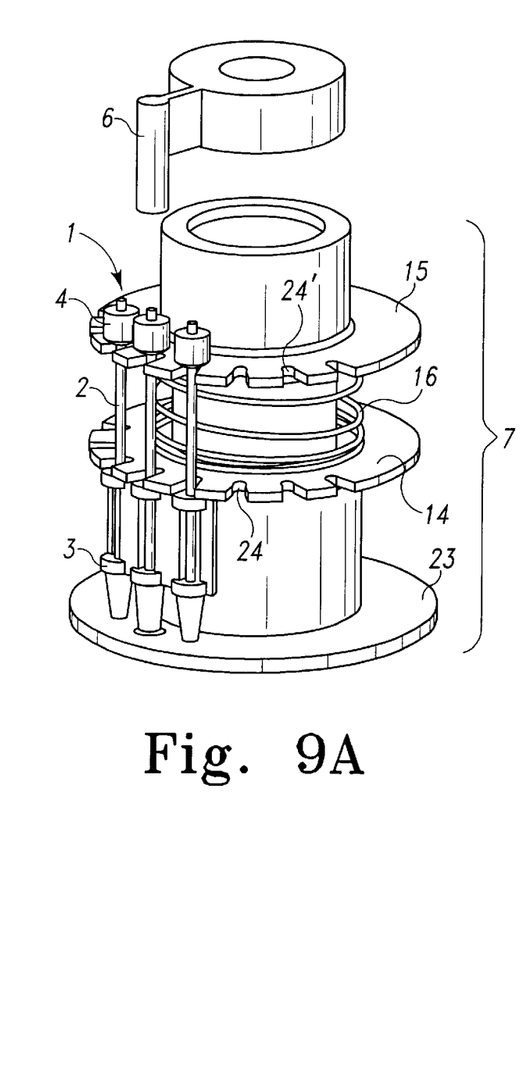

FIG. 9 shows a schematic diagram of a further alternative embodiment of the system according to the invention (FIG.

Figure 9B:
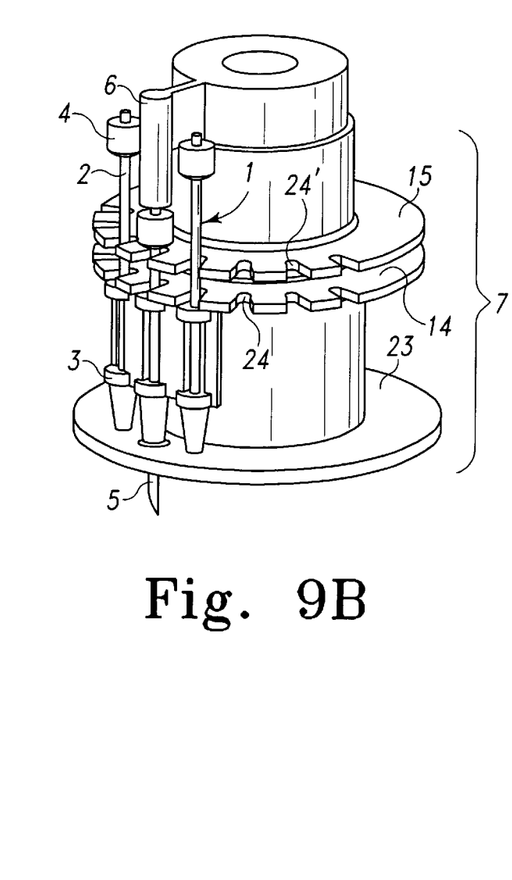

9A before and after carrying out the lancing movement; FIG. 9B during the lancing movement). In this case the lancets (1) are moved essentially in a circle around the retraction device (7). The lancets (1) or the corresponding lancet formations composed of several lancets correspond essentially to those of FIGS. 4 and 5. The drive method corresponds to that of FIGS. 6 to 8: the lancets (1) are moved by a drive element (6) from their resting position into the lancing position. In this process the head (4) of the lancet (1) interacts with the movable part (15) of the retraction device (7). The movable part (15) moves in this process towards the stationary part (14) and compresses a spiral spring (16). In this case the lancets (1) are laterally fixed and thus guided in the area of the exposed needle (2) through cut-outs (24) in the stationary and movable parts (14, 15) of the return device (7) which in this case have the shape of a gear rim. The return device (7) has a rim provided with an opening which serves as a stop (23) for the lancet body (3) and ensures that the lancet body (3) cannot move together with the lancet needle (2) during the lancing movement.

Figure 10A:
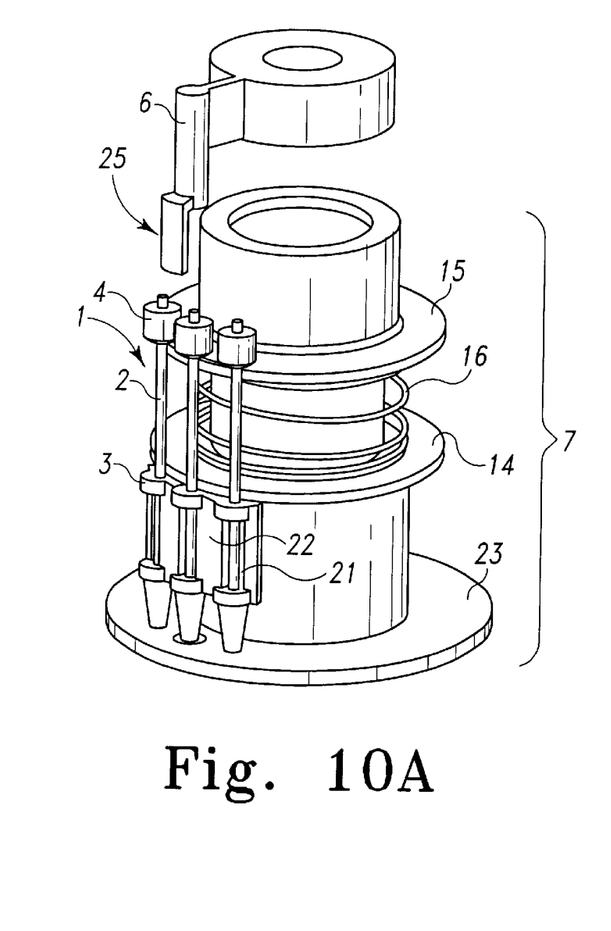
Figure 10B:
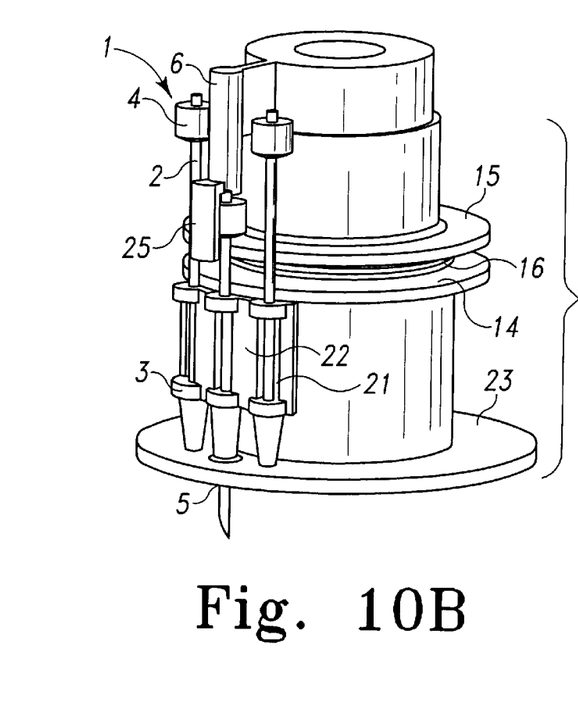
Figure 11A:
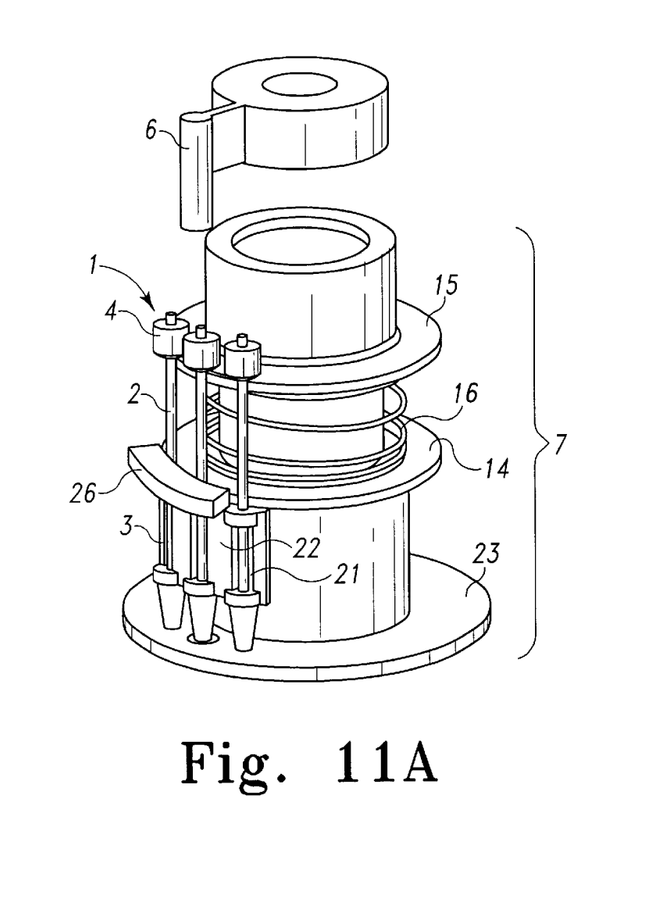
Figure 11B:
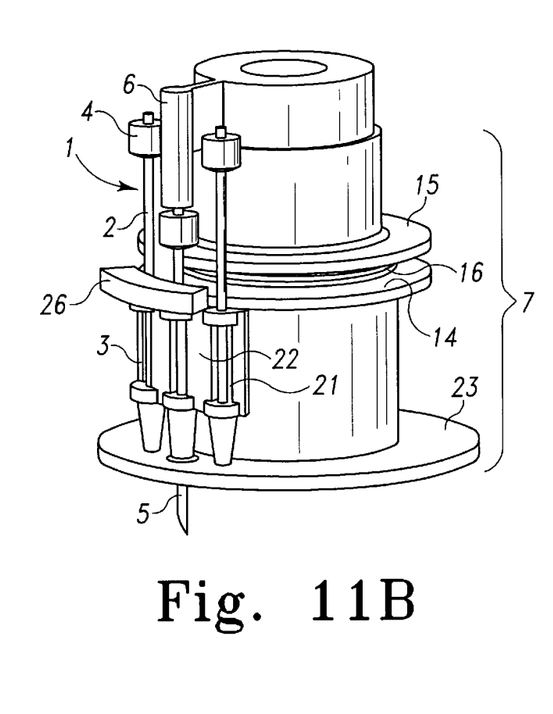

The gear-rim-shaped parts (14, 15) of the return device (7) of this embodiment can also be used to further transport the lancets. FIG. 10 also shows two detailed drawings (FIG. 10A: before and after carrying out the lancing movement; FIG. 10B during the lancing process) of a variant of the embodiment of FIG. 9. In contrast to the embodiment shown in FIG. 9 the parts (14, 15) of the return device (7) have no notches. In this case the lancet needle (2) is guided during the lancing process by the guide element (25) of the drive element (6). FIG. 11 also shows two detailed drawings (FIG. 11A: before and after carrying out the lancing movement; FIG. 10B during the lancing process) of a variant of the embodiment of FIG. 10. In contrast to the embodiment shown there, the lancet needle (2) is in this case guided by means of a guide element (26) which for example can be attached to a housing wall of an appropriate lancing magazine.

Of course all the shown embodiments can contain more or fewer lancets (1) than those shown. It is also possible to interchange the various lancet shapes in the illustrated examples or to use different lancets (1) to those shown.

What is claimed is:

1. A system for storing and providing lancets for collecting body fluids comprising
   i) a plurality of longitudinal, essentially needle-shaped lancets, each lancet having a tip;
   ii) a storage area to store the lancets laterally adjacent to each other;
   iii) a withdrawal area to guide at least the tip of one lancet out of the system during a lancing process;
   iv) a transport unit for transporting the lancets from the storage area into the withdrawal area,
   v) a drive unit including a drive element for moving a lancet in the withdrawal area from a resting position to a lancing position during the lancing process; and
   vi) a retraction device separate from the drive unit and the transport unit, the retraction device being located in the withdrawal area for interaction with each lancet when located in the withdrawal area for automatically moving the lancet after completion of the lancing process from the lancing position back into the resting position.

2. A system as claimed in claim 1, wherein the lancet includes an end opposite to the tip having an element to be gripped by the retraction device.

3. A system as claimed in claim 1, wherein the retraction device contains a spring mechanism.

4. A system as claimed in any of claims 1–3, wherein the lancets are stored in a magazine.

5. A system as claimed in claim 4, wherein the magazine contains the retraction device.

6. A lancet for use in a system as claimed in claim 1 or 2 comprising a lancet needle and a lancet body partially surrounding the lancet needle.

7. A system according to claim 3 wherein the spring mechanism comprises a leaf spring.

8. A system according to claim 3 wherein the spring mechanism comprises a spiral spring.

9. A process for temporarily driving the tip of an essentially needle-shaped lancet out of a system for storing and providing lancets, the system including a drive element-, a transfer mechanism for moving the lancets from a storage position, and a retraction device that is separate from the drive element and from the transfer mechanism, the process comprising the steps of:
   moving a lancet laterally from a storing position into a resting position,
   driving the drive element for its resting position towards the lancet located in the resting position thereby propelling the lancet longitudinally from its resting position until it reaches its lancing position, and
   subsequently automatically returning the lancet to its resting position with the aid of the separate retraction device.

10. The process as claimed in claim 9, wherein the returning step also moves the drive element towards its resting position.

11. A lancet magazine for storing lancets comprising
   a storage area for storing a plurality of longitudinal, essentially needle-shaped lancets, the lancets being stored laterally side-by-side; and
   a withdrawal area wherein at least a tip of a lancet may be extended out of the magazine during a lancing process; and
   a transport unit to transport the lancets from the storage area into the withdrawal area;
   the withdrawal area also including an area for receiving a drive element for driving a lancet in the withdrawal area out of the magazine during a lancing process; and an area for receiving a retraction device separate from the transport unit and the drive element for interaction with any lancet located in the withdrawal area to automatically move the lancet from a lancing position back into a resting position after the lancing process has been completed.

12. A lancet magazine as claimed in claim 11, wherein each lancet in the magazine includes an end opposite to the tip having an element that can be gripped by the retraction device.

13. A lancet magazine as claimed in claim 11, wherein the retraction device contains a spring mechanism.

14. A lancet magazine according to claim 13 wherein the spring mechanism comprises a leaf spring.

15. A lancet magazine according to claim 13 wherein the spring mechanism comprises a spiral spring.

16. A lancet magazine as claimed in any of claims 11, 12, or 13 wherein the transport unit comprises a gear to interact with the lancets in the magazine.

17. A lancet magazine as claimed in claim 16 wherein the transport unit further comprises a motor coupled to the gear.

18. A lancet magazine as claimed in claim 17 wherein the transport unit further comprises an energy supply coupled to the motor.

19. A lancing device suitable for use in a system for storing and providing lancets comprising
   i) a storage area to store the lancets;
   ii) a withdrawal area to guide at least a tip of each lancet out of the system during the lancing process;

iii) a transport unit to transport lancets from the storage area to a Testing position in the withdrawal area;

iv) a drive unit area having a drive element separate from the transport unit, the drive unit being movable to carry out a lancing process wherein a lancet in the withdrawal area moves from its resting position into a lancing position; and v) a retraction device separate from the drive unit and the transport unit for interaction with any lancet located in the withdrawal area to automatically move the lancet, after completion of the lancing process, from its lancing position back into its resting position.

* * * * *